(12) United States Patent
Wright

(10) Patent No.: US 7,875,100 B2
(45) Date of Patent: Jan. 25, 2011

(54) SERVICE LIFE INDICATOR FOR CHEMICAL FILTERS

(75) Inventor: Michael W. Wright, Renton, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 12/784,754

(22) Filed: May 21, 2010

(65) Prior Publication Data

US 2010/0231196 A1  Sep. 16, 2010

Related U.S. Application Data

(62) Division of application No. 11/847,431, filed on Aug. 30, 2007, now Pat. No. 7,749,303.

(51) Int. Cl.
*B01D 46/46* (2006.01)

(52) U.S. Cl. .................. 95/8; 95/25; 96/18; 96/26; 96/109; 96/111; 96/117; 96/417; 55/DIG. 34; 73/1.06

(58) Field of Classification Search .......... 95/8, 95/25; 96/18, 26, 109, 111, 117, 417; 55/DIG. 34; 73/1.06
See application file for complete search history.

(56) References Cited

U.S. PATENT DOCUMENTS

| | | | |
|---|---|---|---|
| 3,999,122 A | 12/1976 | Winstel et al. |
| 4,312,228 A | 1/1982 | Wohltjen |
| 4,472,356 A | 9/1984 | Kolesar, Jr. |
| 4,543,112 A | 9/1985 | Ackley et al. |
| 4,572,178 A | 2/1986 | Takase et al. |
| 4,714,486 A | 12/1987 | Silverthorn |
| 4,886,056 A | 12/1989 | Simpson |
| 4,971,052 A | 11/1990 | Edwards |
| 5,012,668 A | 5/1991 | Haworth |
| 5,022,901 A | 6/1991 | Meunier |
| 5,235,235 A | 8/1993 | Martin et al. |
| 5,287,035 A | 2/1994 | Carroll et al. |
| 5,315,987 A | 5/1994 | Swann |
| 5,640,952 A | 6/1997 | Swann et al. |
| 5,861,053 A | 1/1999 | Noritake et al. |
| 6,340,024 B1 | 1/2002 | Brookman et al. |
| 6,497,756 B1 | 12/2002 | Curado et al. |
| 6,758,212 B2 | 7/2004 | Swann |
| 7,013,891 B2 | 3/2006 | Richardson et al. |
| 2005/0132681 A1 | 6/2005 | Chu |
| 2007/0018836 A1 | 1/2007 | Richardson |

*Primary Examiner*—Robert J Hill, Jr.
*Assistant Examiner*—Christopher P Jones
(74) *Attorney, Agent, or Firm*—McNees Wallace & Nurick LLC

(57) ABSTRACT

A method is provided for indicating the useful service life of a gas filtration and purification system comprising steps of embedding two or more mass-responsive electronic sensors (e.g., surface acoustic wave devices) in a sorbent bed of a filtration cartridge, wherein the mass-responsive electronic sensors are coated with a non-conductive absorptive organic polymer; passing a gas containing a volatile chemical of interest through the filtration cartridge and in contact with the two mass-responsive electronic sensors; and measuring a difference in an electronic property between the two mass-responsive electronic sensors. In such a manner, the two mass-responsive electronic sensors act as internal references with respect to each other, thereby eliminating variations in temperature, interferents, pressure, and the like. When the volatile compound is no longer retained by the sorbent bed, a difference electronic properties of the mass-responsive sensors indicates that the filtration cartridge should be replaced.

20 Claims, 4 Drawing Sheets

SERVICE LIFE INDICATOR FOR CHEMICAL FILTERS

CROSS-REFERENCE TO RELATED APPLICATIONS

This patent application is a divisional of U.S. patent application Ser. No. 11/847,431 now allowed as U.S. Pat. No. 7,749,303 B2, filed on Aug. 30, 2007.

FIELD

Provided herein are an apparatus and method for monitoring the service life of gas filtration systems, wherein the apparatus includes an electronic indicator of useful service life.

BACKGROUND

Filters used in air purification systems must be periodically replaced after a certain period of operation, i.e., at the end of their service life, when they have deteriorated to the point of ineffectiveness. Adsorption cartridges should be replaced in due time, because a deteriorated filter cartridge is not effective in filtering out harmful substances from air. Replacement of adsorption cartridges usually takes place after contaminant break through, pressure drop, or after a certain operating period specified by the manufacturer. In order to be on the safe side, the life of such an adsorption cartridge specified by the manufacturer is determined on the basis of the most unfavorable operating conditions.

A disadvantage of this procedure is that in many instances the adsorption cartridges are replaced long before the end of their useful life, because the cartridges have been used under conditions much more favorable than those assumed by the manufacturer in determining the maximum permissible service life. In addition, administering a cartridge change schedule can be time-consuming, unnecessarily expensive, and cumbersome. Furthermore, contaminants, their concentration levels, temperature, and humidity all affect useful service life, and these variable factors are not adequately addressed by a time-based cartridge replacement schedule.

Real-time end of service life indicators provide an easier and more accurate way than cartridge replacement schedules to determine the service life of gas and vapor cartridges. Colorimetric indicators are available for some filtration cartridges. For example, a colorimetric indicator sensitive to mercury vapor gradually changes color when exposed to it. When the changing color matches the color guide on the cartridge exterior, it is time to change the cartridge.

A need exists, however, for a general method of indicating the useful service life of a gas filtration and purification system, especially a method and related equipment that provide an electronic indication of service life without the need to account for signal drift or interferents.

SUMMARY

A method is provided for indicating the useful service life of a gas filtration and purification system comprising steps of embedding two mass-responsive electronic sensors (e.g., surface acoustic wave devices) in a sorbent bed of a filtration cartridge, wherein the mass-responsive electronic sensors are coated with a non-conductive absorptive organic polymer; passing a gas containing a volatile chemical of interest through the filtration cartridge and in contact with the two mass-responsive electronic sensors; and measuring a difference in an electronic property between the two mass-responsive electronic sensors. In such a manner, the two mass-responsive electronic sensors act as internal references with respect to each other, thereby eliminating variations in temperature, interferents, pressure, and the like. When the volatile compound is no longer retained by the sorbent bed, a difference in electronic properties between the mass-responsive sensors indicates that the filtration cartridge should be replaced.

Also provided is an end of service life indicator for a gas filtration and purification system comprising a housing of one or more walls and two or more openings, the openings being of sufficient size and permeability to permit gas to pass through, and the housing defining a gas passageway between said openings; two mass-responsive electronic sensors (e.g., SAW devices) situated within said housing and along said gas passageway; and a solid sorbent (e.g., activated charcoal) situated between the mass-responsive electronic sensors and within said housing. Such an end of service life indicator may have several advantageous features, for example, small size, low cost of manufacture and maintenance, and compatibility with existing canister filtration systems.

Also provided is a gas filtration and purification system comprising a filtration cartridge that contains a particulate filter (e.g., a HEPA filter); a volatile compound purifier (e.g., activated charcoal); and an end of service life indicator, which comprises a housing of one or more walls and two or more openings, the openings being of sufficient size and permeability to permit gas to pass through, and the housing defining a gas passageway between said openings, two mass-responsive electronic sensors situated within the housing and along said gas passageway, and a solid sorbent situated between said mass-responsive electronic sensors and within the housing.

Real-time end of service life indicators as described herein eliminate the guesswork involved in estimating cartridge change schedules, thereby making users increasingly confident of being adequately protected. They also prevent cartridges from being discarded prematurely and reducing or eliminating the requirements for calculating and administering change schedules. Reduced or eliminated use of expensive and cumbersome supplied-air respirators facilitate maneuverability and increase the physical comfort of workers. In addition to reducing the costs of cartridge change schedules, the elimination of some supplied-air respirators saves on the costs of supplied-air systems, including the acquisition and maintenance of associated equipment.

Other features and advantages of the present invention will be apparent from the following more detailed description taken in conjunction with the accompanying drawings, which illustrate, by way of example, some principles of the invention.

Figure 1:
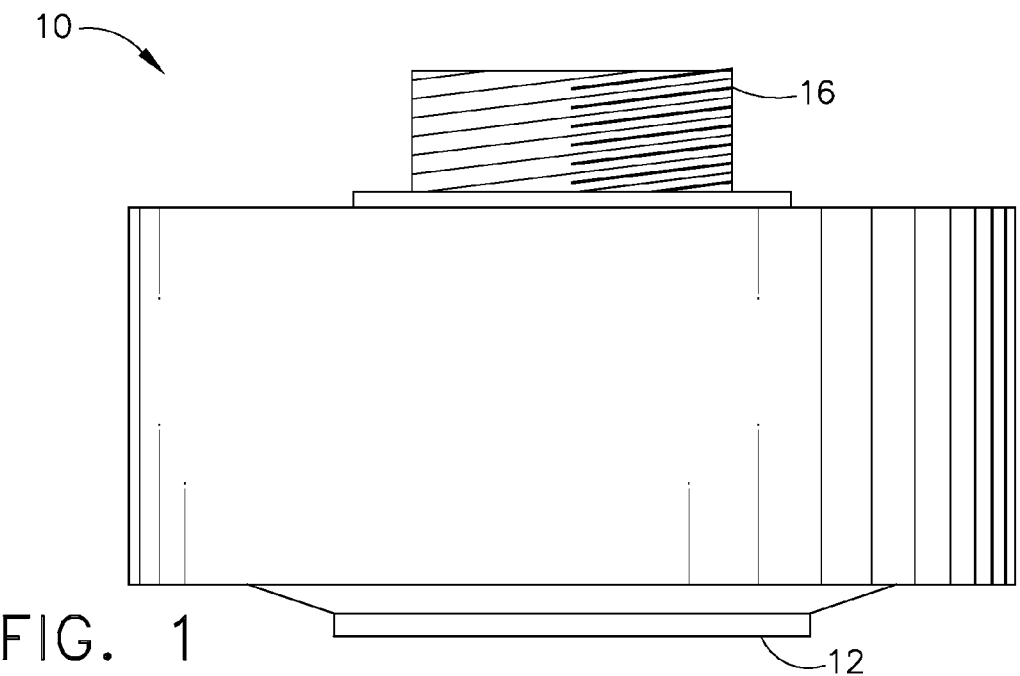
FIG. 1 illustrates an example gas filtration cartridge.

The various components and features illustrated in the drawings are not necessarily drawn to scale.

DETAILED DESCRIPTION

Air purification filters remove undesirable chemicals from the air by sorption into or onto filter media. A finite operating time exists before the filter media saturates and is incapable of removing chemicals from the air. When saturation occurs, the filter must be replaced or reactivated before the air can again be purified. Currently, no general methods exist that permit the rapid determination of filter media saturation (i.e., an end of service life indicator). Filters must be replaced at specified time limits that are based on generous safety margins. Furthermore, the filter user may be exposed to non-purified air (e.g., penetrating chemicals) if the remaining filter media saturates during use. Previous attempts to develop an end of service life indicator for gas filtration systems have been hampered by the search for materials that react to specific undesirable chemicals (e.g., that are sensitive to and specific to the chemical of interest) and by the need for the indicator to be of small size and weight, as well as inexpensive enough to be disposed of with the filter.

Figure 2:
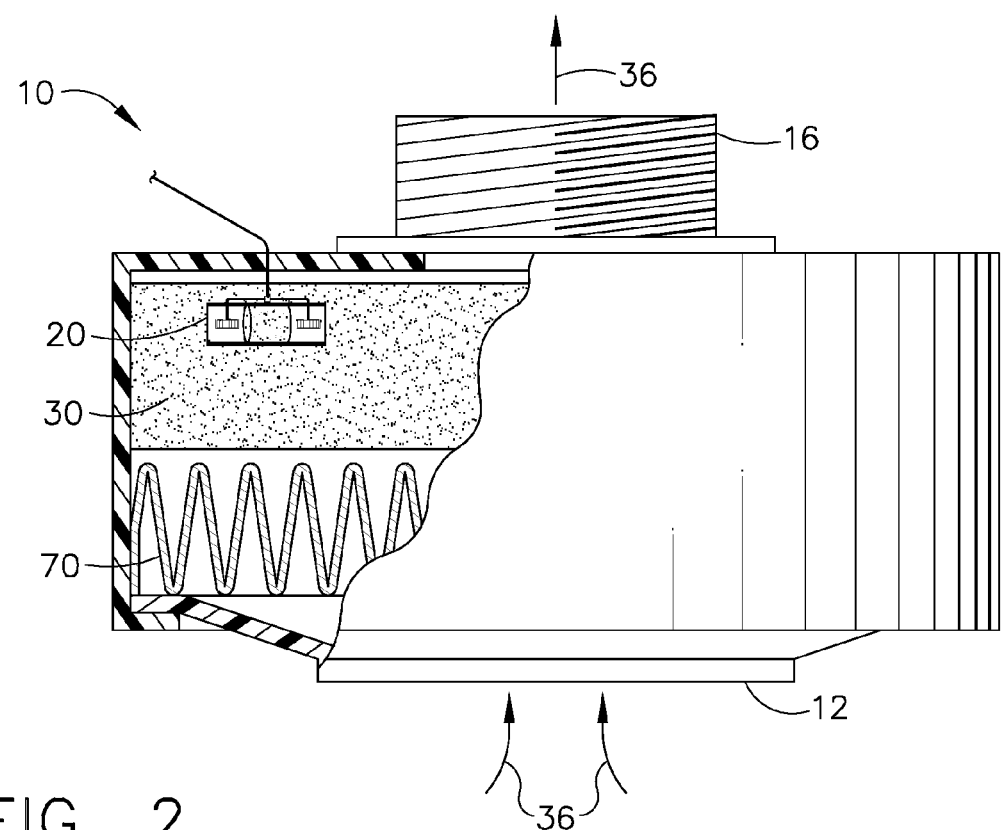
FIG. 2 illustrates a cut-away view of an example gas filtration cartridge.

Provided herein are small, reliable, low-cost filter end of service life indicators that warn the user when the sorption ability of filter media is approaching capacity. Referring to the attached drawings, FIG. 1 illustrates an example embodiment, which includes gas filtration cartridge 10, having inlet 12 and threaded outlet 16. FIG. 2 is a cut-away view of gas filtration cartridge 10, including particulate filter 70 (e.g., a HEPA filter) and sorbent bed 30, which comprises a volatile compound purifier such as activated charcoal and embedded end of service life indicator 20. During operation, gas 36 (which is contaminated with a chemical of interest) flows through inlet 12, particulate filter 70, sorbent bed 30, and finally through threaded outlet 16. As sorbent bed 30 becomes saturated, it loses its capacity to remove the chemical of interest, and eventually end of service life indicator 20 becomes exposed to it, whereupon indicator 20 alerts the user that filtration cartridge 10 should be replaced.

In an example embodiment, end of service life indicator 20 is placed deep in sorbent bed 30 and includes two mass-responsive electronic sensors separated by small volumes of filter media. The mass-responsive electronic sensors, discussed in detail herein below, are each coated with a non-conductive absorptive organic polymer that selectively absorbs a chemical of interest (e.g., a toxin) from gas 36 as it passes through filtration cartridge 10. Because two identical sensors are used, they both act as internal references with respect to each other, thereby eliminating variations in temperature, interferents, pressure, electric power supply, and other ambient conditions. Preferably, absorption of a chemical of interest onto a sensor is the sole cause of a perturbation in its electronic properties.

The end of service life indicator signals that the filter is nearly exhausted when a sensor detects that an undesirable chemical has penetrated the filter bed to the depth of the sensor. In this condition, one sensor is exposed to a chemical of interest, while the other sensor element is clean due to the sorbent media between the sensors. A mismatch in electronic output signals from the sensors indicates chemical penetration to the depth of the sensor(s). Four possible mismatch conditions may occur:

|  | First Sensor | Second Sensor |
| --- | --- | --- |
| Example A | Baseline | Baseline |
| Example B | Baseline | Shift |
| Example C | Shift | Baseline |
| Example D | Shift | Shift |

Example A occurs only if no chemicals are present (or if chemicals are present but the sensors have shifted exactly equal and opposite due to other effects, an extremely unlikely situation), in which case the warning mechanism is not triggered. Examples B and C may occur if one sensor has been exposed to a chemical of interest that have been sorbed by the filter media that shields the second sensor (or if the electronic output signals of the sensors drift unequally, which is extremely unlikely). Such a mismatch in electronic output signals indicates chemical penetration at least to location of the end of service life indicator within the filtration media, and the warning mechanism is triggered. Example D may occur if both sensors frequency shifts equally due to external causes, or if chemical vapors are present at both sensors, which could be a result of chemicals not being sorbed by the filter media (and therefore presumably not being of interest) or after the separating media is saturated.

Accordingly, a method is provided herein for indicating the useful service life of a gas filtration and purification system comprising steps of embedding a plurality (e.g., two or more) mass-responsive electronic sensors in a sorbent bed of a filtration cartridge, wherein the mass-responsive electronic sensors are coated with a non-conductive absorptive organic polymer; passing a gas containing a volatile chemical of interest through the filtration cartridge and in contact with the two mass-responsive electronic sensors; and measuring a difference in an electronic property between the two mass-responsive electronic sensors. Divergent readings from the mass-responsive electronic sensors indicates that the filtration cartridge should be replaced.

In such a manner, the two mass-responsive electronic sensors act as internal references with respect to each other, thereby eliminating triggers by variations in temperature, interferents, pressure, and the like. When the chemical of interest is no longer retained by the sorbent bed, a difference in electronic properties between the mass-responsive sensors indicates that the filtration cartridge should be replaced. In an embodiment, the chemical of interest is absorbed onto at least one of the mass-responsive electronic sensors thereby causing a change in the electronic property of the sensor. In another embodiment, the two mass-responsive electronic sensors are identical and a change in the difference in the electronic property indicates the end of remaining service life of the filtration cartridge.

Figure 3:
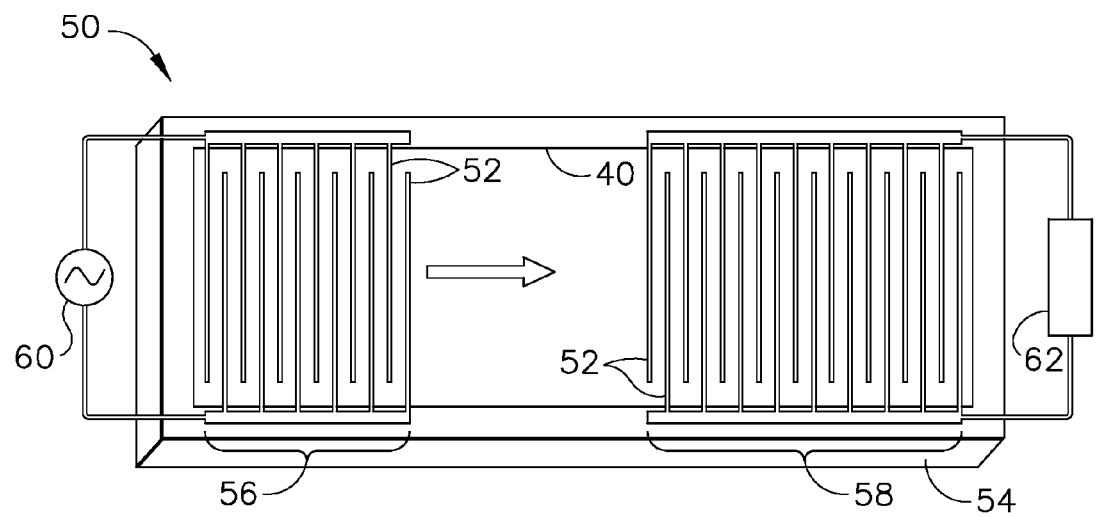
FIGS. 3 and 4 illustrate an example SAW device.
Figure 4:
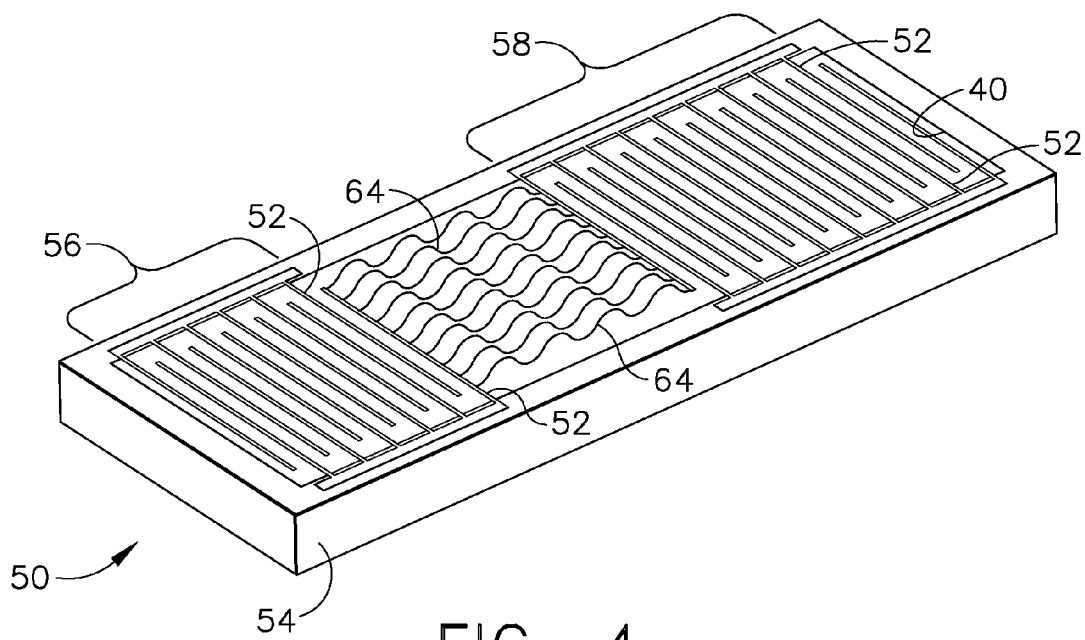

In an example embodiment, the two mass-responsive electronic sensors used in the end of service life indicator are surface acoustic wave ("SAW") devices. A top view of an example SAW device is depicted in FIG. 3, and a perspective view is depicted in FIG. 4. Many SAW devices used for detecting chemical substances are known in the art and commercially available.

Referring to the drawings, SAW device 50 typically comprises two pairs of interdigital (or interleaved) electrodes 52 disposed on the surface of piezoelectric substrate 54 (e.g., lithium tantalate, lithium niobate, or quartz) or another suitable substrate, formed at opposite ends thereof. Conventional photolithographic and etching techniques are used to produce the electrode pattern. When input radio frequency (RF) voltage 60 is applied to the electrode pair (e.g., input transducer 56) on one end of device 50, Rayleigh surface acoustic wave 64 is generated and propagates over substrate 54 toward the other pair of electrodes (e.g., output transducer 58), which produces corresponding output RF voltage 62. Because surface acoustic wave 50 propagates by mechanical deformation of piezoelectric substrate 54 in the region between the pairs of electrodes 52, the polymeric material applied as coating 40 on that region of substrate 54 affects certain characteristic parameters of surface acoustic wave 64, such as its amplitude, velocity, and phase. Furthermore, when the material is exposed to a chemical substance, e.g., a vapor, these parameters change as the chemical substance is absorbed or adsorbed by coating 40. The change in mass of coating 40 resulting from its absorption of a chemical of interest causes a proportional change in the phase or frequency of RF signal output 62 from the electrodes that are excited by surface acoustic wave 64. Similarly, the amplitudes of surface acoustic wave 64 and of output signal 62 may change in proportion to the amount of the chemical substance that is absorbed.

By selecting the material coating applied to the substrate, which is typically a non-conductive absorptive organic polymer, for its characteristic solubility in a desired chemical substance, the SAW device can be used to detect that specific chemical substance. Since other operating parameters, such as ambient temperature, may effect the signal output from the chemical sensor SAW device, the signal output from a SAW device is compared to an identical internal reference SAW device. Since both of the SAW devices are exposed to the same environment, any difference between their output signals is indicative of absorption of a chemical substance by one of the SAW devices. The polymeric coating changes the phase, delay, and amplitude of a surface acoustic wave propagating over the substrate between overlapping interlaced fingers of the first and second electrodes, as a function of the amount of the substance absorbed by the coating comprising the region through which the surface acoustic wave passes.

In an embodiment, the non-conductive absorptive organic polymer may be selected from the group consisting of polydienes, polyalkenes, polyacrylics, polymethacrylics, polyvinyl ethers, polyvinyl thioethers, polyvinyl alcohols, polyvinyl ketones, polyvinyl halides, polyvinyl nitriles, polyvinyl esters, polystyrenes, polyarylenes, polyoxides, polycarbonates, polyesters, polyanhydrides, polyurethanes, polysulfonates, polysiloxanes, polysulfides, polythioesters, polysulfones, polysulfonamides, polyamides, polyureas, polyphosphazenes, polysilanes, polysilazanes, polyfuran tetracarboxylic acid diimides, polybenzoxazoles, polyoxadiazoles, polybenzothiazinophenothiazines, polybenzothiazoles, polypyrazinoquinoxalines, polypyromellitimides, polyquinoxalines, polybenzimidazoles, polyoxindoles, polyoxoisoindolines, polydioxoisoindolines, polytriazines, polypyridazines, polypiperazines, polypyridines, polypiperidines, polytriazoles, polypyrazoles, polypyrrolidines, polycarboranes, polyoxabicyclononanes, polydibenzofurans, polyphthalides, polyacetals, polyanhydrides, carbohydrates, and combinations thereof. For example, the organic polymer may be selected from the group consisting of fluoropolyol, polyethylene maleate, polydimethylsiloxane, and combinations thereof.

The polymer coating may be selected for particular chemicals of interest specific to the intended application or use. Some example chemicals of interest include broad ranges of chemical classes such as organics including, for example, alkanes, alkenes, alkynes, dienes, alicyclic hydrocarbons, arenes, alcohols, ethers, ketones, aldehydes, carbonyls, biogenic amines, thiols, polynuclear aromatics and derivatives of such organics, biomolecules such as isoprenes and isoprenoids, fatty acids and derivatives thereof.

Accordingly, some applications include environmental toxicology and remediation, materials quality control and manufacturing, food and agricultural products monitoring and processing, hazardous spill clean up, as well as heavy industrial manufacturing, ambient air monitoring and purification, worker protection, leak detection and identification, oil/gas petrochemical applications, combustible gas protection, $H_2S$ and other hazardous gas protection, emergency response and law enforcement applications, underground (e.g., coal) mining, volatile organic compound (VOC) protection, air quality monitoring, chemical weapons protection for military and civilian applications, air purification systems for aircraft, fermentation process monitoring and control applications, flavor composition and identification, product quality and identification, refrigerant and fumigant detection, perfume and fragrance formulation, product quality testing, refueling operations, shipping container inspection, diesel and gasoline fuel handling, formaldehyde protection, smoke protection, and automatic ventilation control applications (cooking, smoking, etc.), among others.

Also provided is a gas filtration and purification system comprising a filtration cartridge (or any other solid material collector that comprises various types of gas purifying means) that contains a particulate filter; a volatile compound purifier; and an end of service life indicator, which comprises a housing of one or more walls and two or more openings, the openings being of sufficient size and permeability to permit gas to pass through, and the housing defining a gas passageway between said openings, two mass-responsive electronic sensors situated within the housing and along said gas passageway, and a solid sorbent situated between said mass-responsive electronic sensors and within the housing. In an embodiment, the volatile compound purifier and the solid sorbent in a gas filtration and purification system are the same. The gas filtration and purification system may include further components, such as an electric power supply, visual or auditory signaling means (LEDs, buzzers, alarms, lights, sirens, etc.), electric wiring, microprocessors (such as ASICs), sensor software, and the like.

The particulate filter (e.g., particulate solids, etc.) generally has no particular chemical affinity for a constituent of a mixture. Instead, the separation depends on a mechanical entrapment of solid particles because of their relatively large size compared with the interstices or spaces between individual elements of the particulate filter. In an embodiment, the particulate filter is a HEPA (High Efficiency Particulate Apparatus) filter, which is typically made from a non-woven structure and may comprise pleated media, unpleated media or a combination of both.

The volatile compound purifier is typically a solid sorbent, e.g., a solid material that separates one or more constituents (e.g., gas, vapor, etc.) from a gas mixture containing such constituents in a quasi-chemical manner. The action in most instances is that of selective retention (i.e., the sorbent removes only that part of the gas mixture for which it has the greatest affinity). The retained constituent cannot usually be removed by shaking, brushing, or similar mechanical action, but may be removed by heating, pressure reduction, or use of a stripping or denuding fluid. The sorbent may work by chemical absorption (the holding of a constituent by cohesion or capillary action in the pores of a solid) or by adsorption (the ability of a sorbent to hold or concentrate gases, liquids, or dissolved substances upon its surface). Example sorbents may be selected a sorbent from the group consisting of activated carbon, silica, bonded silica, porous polymer beads, magnesium silicate (e.g., FLORISIL®, a registered trademark of U.S. Silica Co.), and combinations thereof.

The type of sorbent is selected based on the intended application. For example, activated carbon is excellent for collecting organic solvent. Silica gel is effective for collecting polarized gaseous materials. Florisil is suitable for collecting chlorinated biphenyl (PCB). Filter paper with 2-pyridyl piperazine impregnated therein may be used for capturing toluene-diisocyanate (TDI); and filter paper with triethanolamine impregnated therein may be used for capturing nitrogen oxide.

Also provided herein is an end of service life indicator for a gas filtration and purification system comprising a housing of one or more walls and two or more openings (e.g., a small piece of plastic tubing), the openings being of sufficient size and permeability to permit gas to pass through, and the housing defining a gas passageway between said openings; two mass-responsive electronic sensors situated within said housing and along said gas passageway; and a solid sorbent situated between the mass-responsive electronic sensors and within said housing. Typically, the openings are constructed of a gas-permeable material (e.g., the openings are in the form of a membrane, frit, or mesh), and the housing is constructed of a gas-impermeable material.

Figure 5:
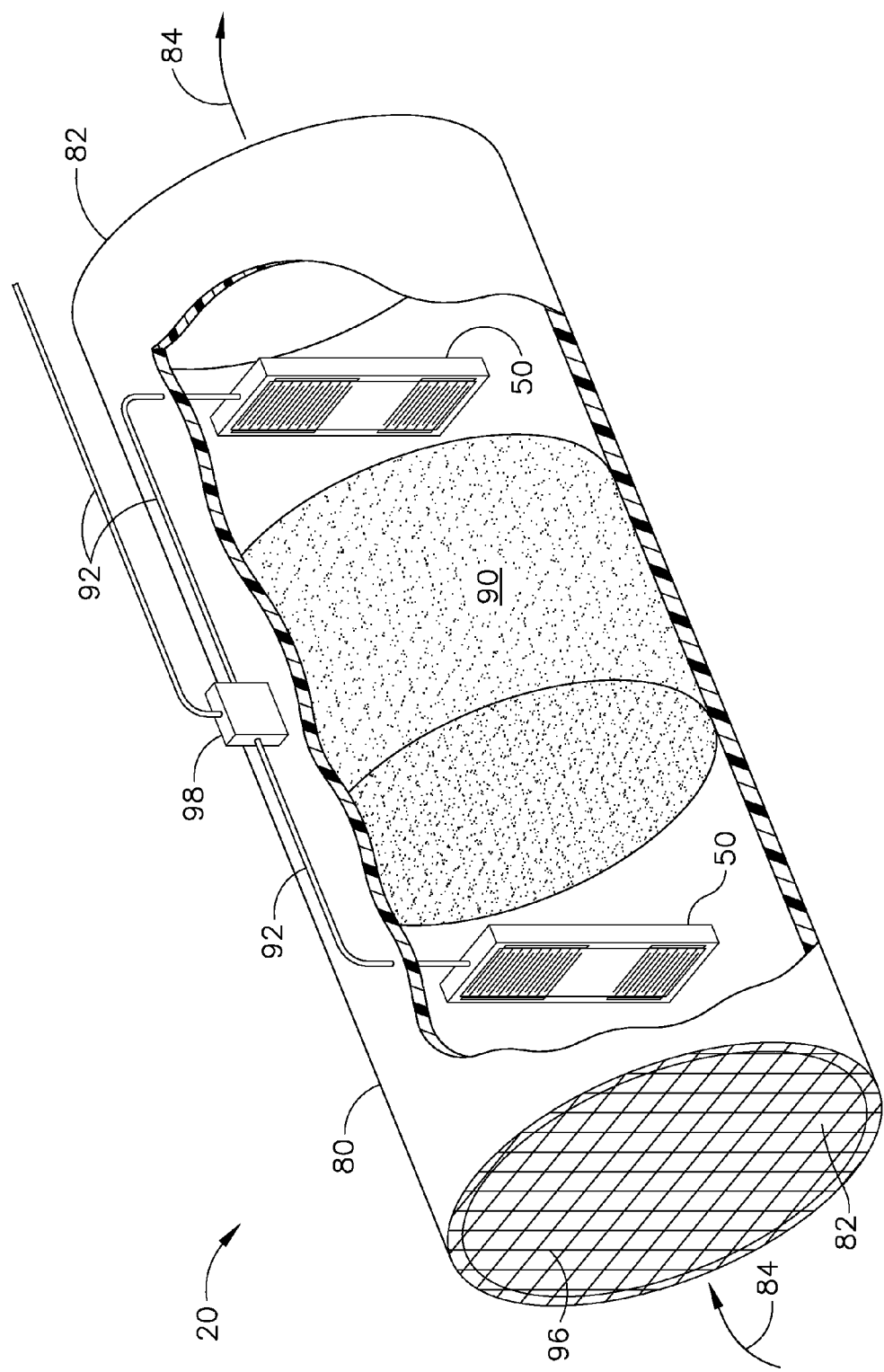
FIGS. 5 and 6 illustrate example end of service life indicators.
Figure 6:
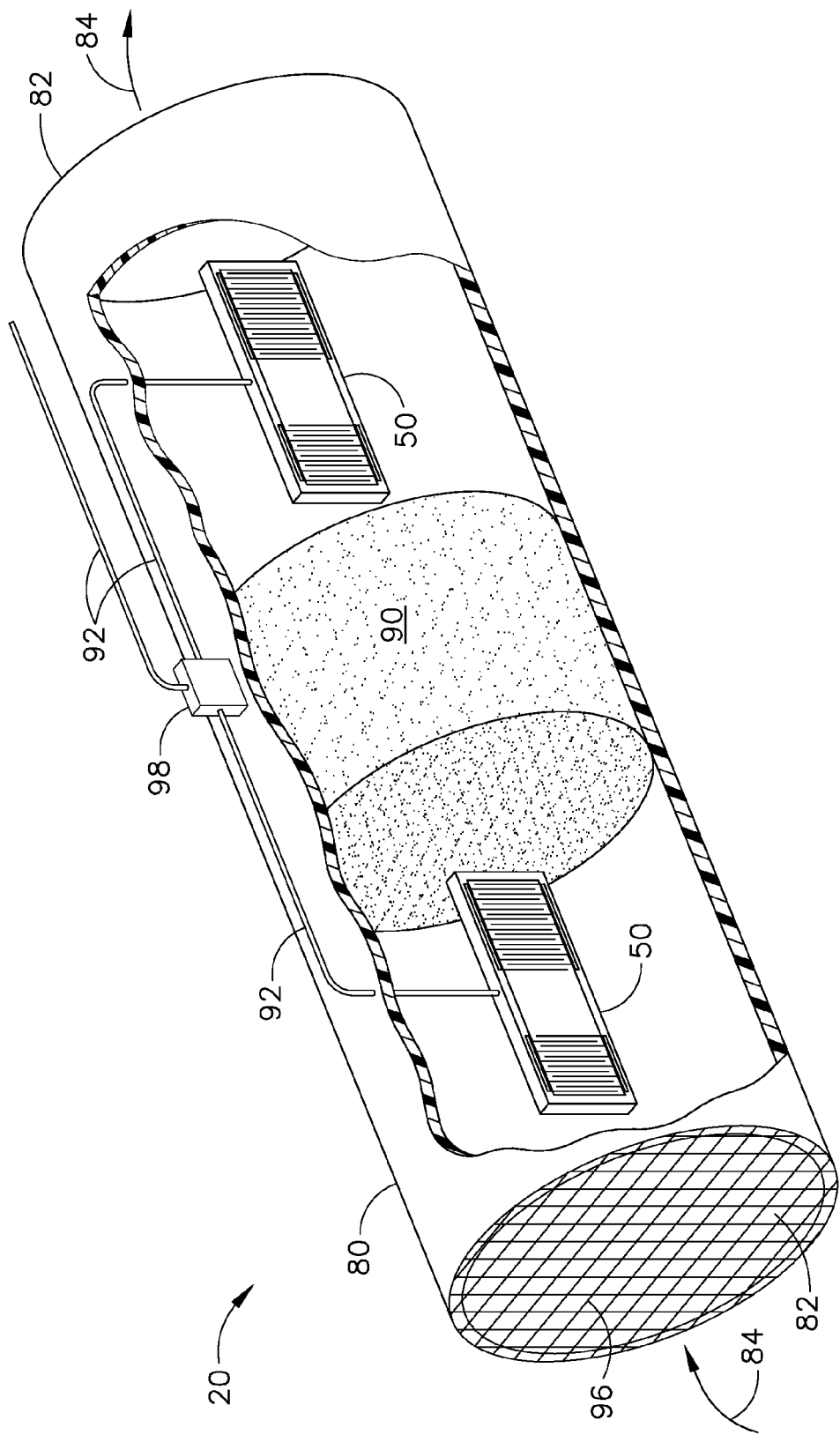

Some example end of service life indicators are depicted in the drawings, attached hereto. As illustrated in FIGS. 5 and 6, end of service life indicator 20 may comprised housing 80, which is in the shape of an elongated cylinder (i.e., a cylinder having a greater length than diameter). The mass-responsive electronic sensors, e.g., SAW devices 50, are situated at distal ends (one device at each end) of housing 80, each of the mass-responsive electronic sensors being proximate to at least one of the openings 82. Gas passageway 84 is formed by cylindrical housing 80 and openings 82, which are covered with mesh 96. A quantity of solid sorbent 90 is situated within housing 80 and between SAW devices 50. Electric wiring 92 provides electric power to SAW devices 50, and permits monitoring of the electronic output signals therefrom. Signal processing unit 98, which monitors any difference between SAW devices 50, may also be provided.

An end of service life indicator may include many other features that are not shown in the Figures. It is important to note that the construction and arrangement of the systems as shown in the various exemplary embodiments are illustrative only. Although only a few embodiments have been described in detail herein, those skilled in the art will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter hereof. For example, elements shown as integrally formed may be constructed of multiple parts or elements, the position of elements may be reversed or otherwise varied, and the nature or number of discrete elements or positions may be altered or varied. Furthermore, the order or sequence of any process or method steps may be varied or re-sequenced according to alternative embodiments. Accordingly, all such modifications are intended to be included within the scope of the appended claims, and other substitutions, modifications, changes and omissions may be made in the design, operating conditions and arrangement of the exemplary embodiments without departing from the scope thereof.

The invention claimed is:

1. A method of indicating service life of a gas filtration and purification system, comprising steps of: embedding a housing comprising a plurality of mass-responsive electronic sensors and sorbent in a sorbent bed of a filtration cartridge, wherein said mass-responsive electronic sensors are coated with a non-conductive absorptive organic polymer; passing a gas containing a volatile chemical of interest through said filtration cartridge and in contact with said two mass-responsive electronic sensors; and measuring a difference in an electronic property between said two mass-responsive electronic sensors.

2. The method according to claim 1, wherein said volatile chemical of interest is absorbed onto at least one of said mass-responsive electronic sensors thereby causing a change in said electronic property.

3. The method according to claim 1, wherein said two mass-responsive electronic sensors are identical and a change in said difference in said electronic property is indicative of remaining service life of said filtration cartridge.

4. The end of service life indicator according to claim 1, wherein said mass-responsive electronic sensors are surface acoustic wave (SAW) devices.

5. The method according to claim 4, wherein each of said SAW devices comprises two pairs of interleaved electrodes disposed on the surface of a piezoelectric substrate.

6. The method according to claim 5, wherein said piezoelectric substrate is selected from the group consisting of lithium tantalate, lithium niobate, and quartz.

7. The method according to claim 1, wherein said non-conductive absorptive organic polymer is selected from the group consisting of polydienes, polyalkenes, polyacrylics, polymethacrylics, polyvinyl ethers, polyvinyl thioethers, polyvinyl alcohols, polyvinyl ketones, polyvinyl halides, polyvinyl nitriles, polyvinyl esters, polystyrenes, polyarylenes, polyoxides, polycarbonates, polyesters, polyanhydrides, polyurethanes, polysulfonates, polysiloxanes, polysulfides, polythioesters, polysulfones, polysulfonamides, polyamides, polyureas, polyphosphazenes, polysilanes, polysilazanes, polyfuran tetracarboxylic acid diimides, polybenzoxazoles, polyoxadiazoles, polybenzothiazinophenothiazines, polybenzothiazoles, polypyrazinoquinoxalines, polypyromellitimides, polyquinoxalines, polybenzimidazoles, polyoxindoles, polyoxoisoindolines, polydioxoisoindolines, polytriazines, polypyridazines, polypiperazines, polypyridines, polypiperidines, polytriazoles, polypyrazoles, polypyrrolidines, polycarboranes, polyoxabicyclononanes, polydibenzofurans, polyphthalides, polyacetals, polyanhydrides, carbohydrates, and combinations thereof.

8. A method of indicating service life of a gas filtration and purification system comprising steps of: embedding a housing comprising two or more mass-responsive electronic sensors and sorbent in a sorbent bed of a filtration cartridge, passing a gas containing a volatile chemical of interest through said filtration cartridge; and measuring an electronic property of said two mass-responsive electronic sensors.

9. The method according to claim 8, wherein said volatile chemical of interest is absorbed onto at least one of said two or more mass-responsive electronic sensors thereby causing a change in said electronic property of at least one of said two or more mass-responsive electronic sensors.

10. The method according to claim 8, wherein said two mass-responsive electronic sensors are identical and a change in said electronic property is indicative of remaining service life of said filtration cartridge.

11. The method according to claim 8, wherein said mass-responsive electronic sensors are surface acoustic wave (SAW) devices.

12. The method according to claim 11, wherein each of said SAW devices comprises two interleaved electrodes disposed on a surface of a piezoelectric substrate, and a non-conductive absorptive organic polymer disposed on the surface between the two interleaved electrodes.

13. The method according to claim 12, wherein said piezoelectric substrate is selected from the group consisting of lithium tantalate, lithium niobate, and quartz.

14. The method according to claim 12, wherein said non-conductive absorptive organic polymer is selected from the group consisting of polydienes, polyalkenes, polyacrylics, polymethacrylics, polyvinyl ethers, polyvinyl thioethers, polyvinyl alcohols, polyvinyl ketones, polyvinyl halides, polyvinyl nitriles, polyvinyl esters, polystyrenes, polyarylenes, polyoxides, polycarbonates, polyesters, polyanhydrides, polyurethanes, polysulfonates, polysiloxanes, polysulfides, polythioesters, polysulfones, polysulfonamides, polyamides, polyureas, polyphosphazenes, polysilanes, polysilazanes, polyfuran tetracarboxylic acid diimides, polybenzoxazoles, polyoxadiazoles, polybenzothiazinophenothiazines, polybenzothiazoles, polypyrazinoquinoxalines, polypyromellitimides, polyquinoxalines, polybenzimidazoles, polyoxindoles, polyoxoisoindolines, polydioxoisoindolines, polytriazines, polypyridazines, polypiperazines, polypyridines, polypiperidines, polytriazoles, polypyrazoles, polypyrrolidines, polycarboranes, polyoxabicyclononanes, polydibenzofurans, polyphthalides, polyacetals, polyanhydrides, carbohydrates, and combinations thereof.

15. The method according to claim 8, wherein a change in said electronic property of one or more of the two or more is indicative of remaining service life of said filtration cartridge.

16. The method according to claim 8, wherein said two or more mass-responsive electronic sensors are identical and a change in said electronic property of one or more of the two or more mass-responsive electronic sensors is indicative of remaining service life of said filtration cartridge.

17. The method according to claim 8, further comprising:
comparing the electronic property of the two or more mass-responsive electronic sensors for a difference in the electronic property of the two or more mass-responsive electronic sensors, the difference in the electronic property of the two or more mass-responsive electronic sensors indicating an end of service life of the gas filtration and purification system.

18. The method according to claim 8, further comprising:
separating the two or more mass-responsive electronic sensors with a quantity of sorbent.

19. The method according to claim 8, further comprising:
disposing at least two of the two or more mass-responsive electronic sensors at unequal distances from an entrance of the gas filtration and purification system.

20. The method according to claim 8, further comprising:
providing electronic power to the two or more mass-responsive electronic sensors.

\* \* \* \* \*